(12) United States Patent
Petersen et al.

(10) Patent No.: US 7,271,273 B2
(45) Date of Patent: Sep. 18, 2007

(54) METHOD FOR THE PREPARATION OF CITALOPRAM

(75) Inventors: Hans Petersen, Vanløse (DK); Michael Harold Rock, Hvidovre (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 11/285,922

(22) Filed: Nov. 23, 2005

(65) Prior Publication Data

US 2006/0079700 A1   Apr. 13, 2006

Related U.S. Application Data

(60) Division of application No. 10/186,337, filed on Jun. 27, 2002, now abandoned, which is a continuation of application No. PCT/DK99/00740, filed on Dec. 30, 1999.

(51) Int. Cl.
C07D 307/54   (2006.01)

(52) U.S. Cl. ........................ 549/304; 549/307

(58) Field of Classification Search ............... 549/304, 549/307
See application file for complete search history.

(56) References Cited

U.S. PATENT DOCUMENTS

| | | | |
|---|---|---|---|
| 3,467,675 A | 9/1969 | Petersen et al. | 260/346.2 |
| 4,136,193 A * | 1/1979 | Bogeso et al. | 514/469 |
| 4,650,884 A | 3/1987 | Bogeso | 549/467 |
| 5,296,507 A | 3/1994 | Tanaka et al. | 514/465 |
| 6,020,501 A | 2/2000 | Massonne et al. | 549/307 |
| 6,028,204 A | 2/2000 | Massonne et al. | 549/307 |
| 6,229,026 B1 | 5/2001 | Petersen | 514/469 |
| 6,258,842 B1 | 7/2001 | Petersen et al. | 514/469 |
| 6,291,689 B1 | 9/2001 | Petersen et al. | 549/467 |
| 6,310,222 B1 | 10/2001 | Ikemoto et al. | 549/467 |
| 6,365,747 B1 | 4/2002 | Dall'Asta et al. | 548/146 |
| 6,392,060 B2 | 5/2002 | Petersen et al. | 549/307 |
| 6,403,813 B1 | 6/2002 | Petersen et al. | 549/305 |
| 6,407,267 B1 | 6/2002 | Rock et al. | 549/467 |
| 6,420,574 B2 | 7/2002 | Petersen et al. | 549/467 |
| 6,426,422 B1 | 7/2002 | Petersen et al. | 549/467 |
| 2002/0004604 A1 | 1/2002 | Petersen et al. | 549/462 |
| 2002/0026062 A1 | 2/2002 | Petersen et al. | 549/467 |
| 2002/0028956 A1 | 3/2002 | Weber et al. | 549/307 |
| 2002/0035277 A1 | 3/2002 | Rock et al. | 549/467 |
| 2002/0040153 A1 | 4/2002 | Petersen | 549/467 |
| 2002/0061925 A1 | 5/2002 | Petersen et al. | 514/469 |
| 2002/0077353 A1 | 6/2002 | Petersen et al. | 514/469 |
| 2002/0087012 A1 | 7/2002 | Castellin et al. | 549/467 |

FOREIGN PATENT DOCUMENTS

| | | |
|---|---|---|
| EP | 0 171 943 A1 | 2/1986 |
| EP | 1 095 926 | 5/2001 |
| WO | 98/19511 | 5/1998 |
| WO | 98/19512 | 5/1998 |
| WO | 98/19513 | 5/1998 |
| WO | 99/30548 | 6/1999 |
| WO | 00/11926 | 3/2000 |
| WO | 00/12044 | 3/2000 |
| WO | 00/13648 | 3/2000 |
| WO | 00/23431 | 4/2000 |
| WO | 00/39112 | 7/2000 |
| WO | 00/44738 | 8/2000 |
| WO | 01/45483 | 6/2001 |
| WO | 01/47877 | 7/2001 |
| WO | 01/47909 | 7/2001 |
| WO | 01/51477 | 7/2001 |
| WO | 01/66536 | 9/2001 |

OTHER PUBLICATIONS

U.S. Appl. No. 10/183,958, filed Jun. 25, 2002.
U.S. Appl. No. 10/191,808, filed Jul. 8, 2002.
Levy, L.F., "4-Aminophthalide and Some Derivatives", *J. Chem. Soc.* pp. 867-870 (1931).
Tirouflet J., "Phtalide Substitutes en 5", *Bull. Soc. Sci. de Bretagne* 26:35-43 (1951).
Bigler, Allan et al., "Quantitative Structure-activity Relationships in a Series of Selective 5-HT uptake inhibitors," *Eur. J. Med. Chem.* 3:289-295 (1997).
Forney L., "Reaction of Terephthalic Acid with Formaldehyde in Sulfur Trioxide Media," *J. Org. Chem.* 35:1695-1696 (1970).
Dordor et al., "Reaction of Oxazolines with Phosphorus Oxychloride," *Tetrahedron Letters* 24:1437-1440 (1983).
Barton et al., *Comprehensive Organic Chemistry. The Synthesis and Reactions of Organic Compounds*, vol. 2, pp. 1024-1025.
Harrison, Ian T. et al., *Compendium of Organic Synthetic Methods*, p. 458, John Wiley & Sons (New York: 1971).
Sakakibara, Yasumasa et al., "The Cyanation of Aromatic Halides Catalyzed by Nickel(O) Complexes Generated In Situ, I. Generated Scope and Limitations," *Bull. Chem. Soc. Jpn.* 61: 1985-1990 (1988).

\* cited by examiner

*Primary Examiner*—Patricia L. Morris
(74) *Attorney, Agent, or Firm*—Darby & Darby

(57) ABSTRACT

The invention provides a new and improved method for the preparation of 5-cyano-phtalid, which is a key intermediate in the preparation of the antidepressant compound citalopram.

14 Claims, No Drawings

METHOD FOR THE PREPARATION OF CITALOPRAM

This application is a divisional of U.S. Application Ser. No. 10/186,337 filed Jun. 27, 2002, now abandoned, which is a continuation of International application no. PCT/DK99/00740, filed Dec. 30, 1999. The disclosures of both prior applications is hereby incorporated by reference.

The present invention relates to a method for the preparation of key intermediates in the process for the preparation of the well known antidepressant drug citalopram, 1-[3-(dimethylamino)propyl]-1-(4-fluorophenyl)-1,3-dihydro-5-isobenzofurancarbonitrile.

BACKGROUND OF THE INVENTION

Citalopram is a well known antidepressant drug that has now been on the market for some years and has the following structure:

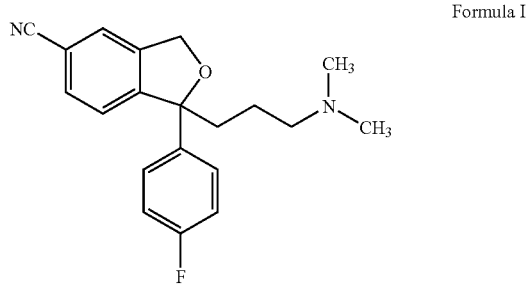

Formula I

It is a selective, centrally acting serotonin (5-hydroxytryptamine; 5-HT) reuptake inhibitor, accordingly having antidepressant activities. The antidepressant activity of the compound has been reported in several publications, eg. J. Hyttel, *Prog. Neuro-Psychopharmacol. & Biol. Psychiat.*, 1982, 6, 277-295 and A. Gravem, *Acta Psychiatr. Scand.*, 1987, 75, 478-486. The compound has further been disclosed to show effects in the treatment of dementia and cerebrovascular disorders, EP-A 474580.

Citalopram can be prepared by several disclosed methods. A method and an intermediate for the preparation of citalopram were described in U.S. Pat. No. 4,650,884. Commercially useful processes are disclosed in International patent application Nos. WO 98019511, WO 98019512 and WO 98019513.

With respect to the above methods for the preparation of citalopram, the process comprising exchange of the 5-bromo group with cyano proved not to be very convenient in commercial scale, since the yield was rather low, the product was impure and, in particular, since it was difficult to separate the resulting citalopram from the corresponding 5-bromo compound.

It has now been found that in a new process for the preparation of citalopram, this key intermediate may be obtained in a high yield as a very pure product by a new catalytic process in which a halogen or a group of the general formula $CF_3$—$(CF_2)_n$—$SO_2$— wherein n is any suitable whole number between 0 and 4, situated in the 5-position of a 3-H-isobenzofuran-1-one, is exchanged with a cyanide group. By obtaining the correct cyanide substitution at an early stage of the citalopram synthesis, the extensive work up of the old cyanide exchange processes of the previous described processes is avoided. The intermediates of the presently described process are easily purified and obtained in very high yields. The key intermediate is then subjected to two successive Grignard reactions, i.e. with 4-fluorophenyl magnesium halogenide and N,N-dimethylaminopropyl magnesium halogenide, respectively, whereby citalopram is obtained.

The preparation of the key intermediate of the invention is described earlier in J. Chem. Soc., 1931, 867 and by Tiroflet, J. in Bull. Soc. Sci. Betagne, 26, 35, 1951. The process for preparation of the compound is a three step synthesis starting from 5-nitro-phtalimide with low yields, especially in the last step of the synthesis.

SUMMARY OF THE INVENTION

Accordingly, the present invention relates to a novel method for the preparation of an intermediate in the preparation of citalopram comprising reacting a compound of Formula IV

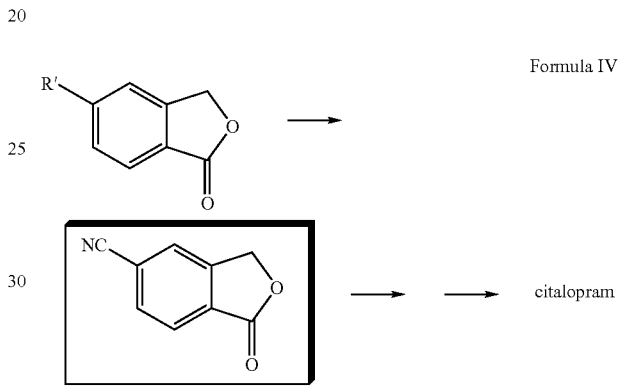

Formula IV wherein R' is Cl, Br, I or a group of the formula $CF_3$—$(CF_2)_n$—$SO_2$—, wherein n is 0-4, with a cyanide source in the presence or absence of a catalyst, whereby 5-cyano-isobenzofuran-1-one is obtained. This intermediate product can be further reacted to citalopram as described above.

The reaction of IV to 5-cyanophtalide may be carried out in more convenient solvents, at a low temperature and at a minimal excess of $CN^-$. The process has environmental advantages in that it only uses small amounts of heavy metals.

The cyano sources may conveniently be selected from a group consisting of cyanide sources such as $(R''_4N)CN$ wherein each R'' represents $C_{1-8}$-alkyl optionally two R'' together with the nitrogen form a ring structure; NaCN, KCN, $Zn(CN)_2$ or $Cu(CN)$.

The reaction of the present invention is performed in the presence or absence of a catalyst. The catalysts are i.e. Ni(0), Pd(0) or Pd(II) catalysts as described by Sakakibara et. al. in *Bull. Chem. Soc. Jpn.*, 61, 1985-1990, (1988). Preferred catalysts are $Ni(PPh_3)_3$ or $Pd(PPh_3)_4$, or $Pd(PPh_3)_2Cl_2$.

In a particularly preferred embodiment, a Nickel(0) complex is prepared in situ before the cyanide exchange reaction by reduction of a Nickel(II) precursor such as $NiCl_2$ or $NiBr_2$ by a metal, such as zinc, magnesium or mangan in the presence of excess of complex ligands, preferably triphenylphosphin.

The Pd or Ni-catalyst is conveniently used in an amount of 0.5-10, preferably 2-6, most preferably about 4-5 mol %.

$Cu^+$ and $Zn^{2+}$ may be added to the reaction mixture in substoichiometric amounts and may function as recycleable cyanide sources, which receives the cyanide from other cyanide sources such as NaCN or KCN. Substoichiometric amounts of $Cu^+$ and $Zn^{2+}$, respectively, means 1-20%, preferably 5-10%.

The reactions may be performed in any convenient solvent as described in Sakakibara et. al. in *Bull. Chem. Soc. Jpn.*, 61, 1985-1990, (1988). Preferred solvents are acetonitrile, ethylacetate, THF, DMF or NMP;

In one aspect of the invention, a compound of Formula IV wherein R is Cl is reacted with NaCN in the presence of a Ni(PPh$_3$)$_3$ which is preferably prepared in situ as described above.

In another aspect of the invention, a compound of formula IV, wherein R is Br or I, is reacted with KCN, NaCN, CuCN or Zn(CN)$_2$ in the presence of Pd(PPh$_3$)$_4$. In a particular aspect of the invention, substoichiometric amounts of Cu(CN) and Zn(CN)$_2$ are added as recycleable cyanide sources.

In another aspect of same invention, the Cu(CN) is the cyanide source and without catalyst. In a preferred embodiment of this invention, the reaction is performed at elevated temperature.

In a particular aspect of this invention, the reaction is performed as a neat reaction i.e. without added solvent.

In another aspect of the invention, the reaction is performed in an ionic liquid of the general formula $R_4N^+$, $X^-$, wherein R are alkyl-groups or two of the R groups together form an ring and $X^-$ is the counterion. In one embodiment of the invention, $R_4N^+X^-$ represents

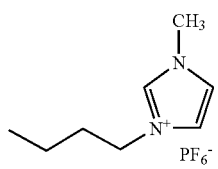

In another particular aspect of this invention, the reaction is conducted with apolar solvents such as benzene, xylene or mesitylene and under the influence of microwaves by using i.e. Synthewave 1000™ by Prolabo. In a particular aspect of this invention, the reaction is performed without added solvent.

The temperature ranges are dependent upon the reaction type. If no catalyst is present preferred temperatures are in the range of 100-200° C. However, when the reaction is conducted under the influence of microwaves the temperature in the reaction mixture may raise to above 300° C. More preferred temperature ranges are between 120-170° C. The most preferred range is 130-150° C.

If catalyst is present, the preferred temperature range is between 0 and 100° C. More preferred are temperature ranges of 40-90° C. Most preferred temperature ranges are between 60-90° C.

Other reaction conditions, solvents, etc. are conventional conditions for such reactions and may easily be determined by a person skilled in the art.

EXAMPLES

The invention is further illustrated by the following examples.

Experimental

Example 1

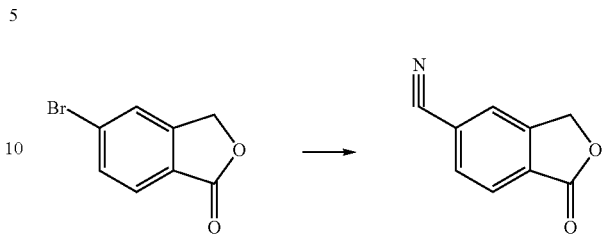

A mixture of Zn(CN)$_2$ (2.4 g, 0.02 mol) and 5-bromo-3H-isobenzofuran-1-one (4.2 g, 0.02 mol) in DMF (80 mL) were stirred at room temperature under an atmosphere of argon for 30 minutes. Then dissolved oxygen was removed by bubbling argon through the reaction mixture for 10 minutes before the addition of tetrakis(triphenylphosphine)palladium (0) (1.2 g, 0.00096 mol,). Then the reaction was heated at 75° C. for 3 hrs, and then the solvent was removed under reduce pressure and the residue poured into water (150 mL). Filtration and followed by drying in vacuo give the crude 5-cyano-3H-isobenzofuran-1-one (2.8 g) (HPLC 95%). An analytical sample was obtained by recrystalisation from acetic acid.

Example 2

A mixture of Zn(CN)$_2$ (0.3 g, 0.00256 mol), NaCN (1 g, 0,02 mol) and 5-bromo-3H-isobenzofuran-1-one (4.2 g, 0.02 mol) in DMF (80 mL) were stirred at room temperature under an atmosphere of argon for 30 minutes. Then dissolved oxygen was removed by bubbling argon through the reaction mixture for 10 minutes before the addition of tetrakis(triphenylphosphine)palladium (0) (1.2 g, 0.00096 mol). Then the reaction was heated at 75° C. for 3 hrs, and then the solvent was removed under reduce pressure and the residue poured into water (150 mL). Filtration and followed by drying in vacuo give the crude 5-cyano-3H-isobenzofuran-1-one (2.7 g) (HPLC 94%). An analytical sample was obtained by recrystalisation from acetic acid.

Example 3

A mixture of 5-bromo-3H-isobenzofuran-1-one (4.2 g, 0.02 mol) and Cu(CN)$_2$ (2.3 g, 0.02 mol) in NMP (60 mL) were stirred at 140 ° C. for 3 hrs. Then solvent was removed by distillation under reduced pressure and the residue was refluxed in water (150 mL) for 10 minutes and allowed to cool to room temperature. Filtration and followed by drying in vacuo give the crude 5-cyano-3H-isobenzofuran-1-one (2.1 g) (HPLC 97%). An analytical sample was obtained by recrystalisation from acetic acid.

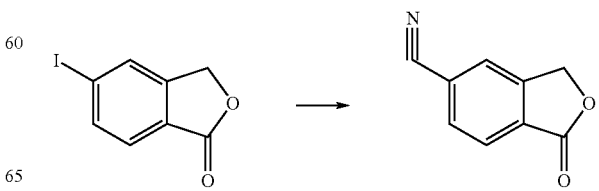

Example 4

A mixture of Zn(CN)₂ (2.4 g, 0.02 mol) and 5-iodo-3H-isobenzofuran-1-one (5.24 g, 0.02 mol) in DMF (80 mL) were stirred at room temperature under an atmosphere of argon for 30 minutes. Then dissolved oxygen was removed by bubbling argon through the reaction mixture for 10 minutes before the addition of tetrakis(triphenylphosphine) palladium (0) (1.2 g, 0.00096 mol). Then the reaction was heated at 75° C. for 3 hrs, and then the solvent was removed under reduce pressure and the residue poured into water (150 mL). Filtration and followed by drying in vacuo give the crude 5-cyano-3H-isobenzofuran-1-one (2.4 g) (HPLC 93%). An analytical sample was obtained by recrystalisation from acetic acid.

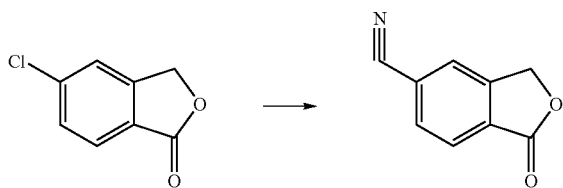

Example 5

Under a nitrogen atmosphere, a mixture of NiCl₂ (0.2 g, 0.0015 mol) and triphenylphosphine (1.6 g, 0.0061 mol) in acetonitrile (80 ml) was heated at reflux for 45 minutes. After cooling to room temperature, zinic powder was added (0.39 g, 0.006 mol) at stirred for 15 minutes before a solution of 5-chloro-3H-isobenzofuran-1-one (3.4 g, 0.02 mol) in THF (40 mL) was added.

After stirring for a further 10 minutes, NaCN (1.1 g, 0.021 mol) was added and the reaction heated at 70° C. for 3 hrs, cooled, diluted with acetonitrile (50 mL), and then filtered through celite. The filtrate was concentrated under reduced pressure and the residue was refluxed in water (150 mL) for 10 minutes and allowed to cool to room temperature. Filtration and followed by drying in vacuo give the crude 5-cyano-3H-isobenzofuran-1-one (2.5 g). An analytical sample was obtained by recrystalisation from acetic acid.

The invention claimed is:

1. A process for the preparation of a compound of the formula

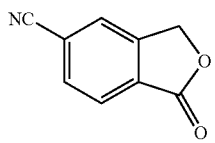

comprising reacting an isobenzofuran-1-one of the formula

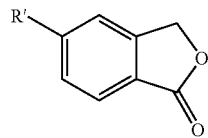

wherein R' is a halogen or $CF_3-(CF_2)_n-SO_2-$, wherein n is 0-7, with a cyanide source optionally in the presence of a catalyst.

2. The process of claim 1 wherein R' is Cl, Br or I.

3. The process of claim 1 wherein R' is $CF_3-(CF_2)_n-SO_2-$, wherein n is 0, 1, 2, 3 or 4.

4. The process of claim 1, wherein the cyanide source is selected from $(R''_4N)CN$ wherein each R" is $C_{1-8}$-alkyl, optionally two R" together with the nitrogen form a ring structure; KCN, NaCN, Zn(CN)₂ or CuCN or combinations thereof.

5. The process of claim 1, wherein $Zn^{2+}$ or $Cu^+$ are added in substoichiometric amounts in combination with another cyanide source.

6. The process of claim 1, wherein the catalyst is selected from Ni(PPh₃)₃, Pd(PPh₃)₄, Pd(dba)₃ or Pd(PPh)₂Cl₂.

7. The process of claim 1, wherein a 5-chloro-isobenzofuran-1-one is subjected to NaCN in the presence of Ni-catalyst.

8. The process of claim 7 wherein the Ni-catalyst is Ni(PPh₃)₃ prepared in situ by subjecting NiCl₂ to a reducing agent, in the presence of PPh₃.

9. The process of claim 8 wherein the reducing agent is Zn.

10. The process of claim 1, wherein a 5-bromo- or 5-iodo-isobenzofuran-1-one is subjected to KCN, NaCN, Zn(CN)₂, or CuCN or combinations thereof in the presence of Pd(PPh₃)₄.

11. The process of claim 1, 2 or 4 wherein a 5-bromo- or 5-iodo-isobenzofuran-1-one is subjected to KCN, NaCN, Zn(CN)₂, or CuCN or combinations thereof and the process is performed without catalysts.

12. The process of claim 10 wherein the reaction is performed in an ionic liquid of the general formula $R_4N^+X^-$ wherein each R represents $C_{1-8}$-alkyl optionally two R" together with the nitrogen form a ring.

13. The process of claim 10 wherein the reaction is performed under the influence of microwaves in an apolar solvent.

14. The process of claim 10 or claim 12 wherein the reaction is performed as a neat reaction.

* * * * *